United States Patent [19]

Kambara et al.

[11] Patent Number: 5,534,703
[45] Date of Patent: Jul. 9, 1996

[54] ELECTROPHORESIS ANALYZER WITH WAVELENGTH SELECTIVE DETECTION

[75] Inventors: Hideki Kambara, Hachiouji; Takashi Anazawa, Kokubunji; Satoshi Takahashi, Kunitachi; Katsuhiko Murakami, Koganei, all of Japan

[73] Assignee: Hitachi, Ltd., Tokyo, Japan

[21] Appl. No.: 220,261

[22] Filed: Mar. 30, 1994

[30] Foreign Application Priority Data

Apr. 7, 1993 [JP] Japan ........................ 5-080927

[51] Int. Cl.$^6$ ............ G01N 27/26; G01N 21/64
[52] U.S. Cl. ........................ 250/458.1; 356/344
[58] Field of Search ............ 250/458.1, 459.1, 250/461.1, 461.2; 204/299 R; 356/344

[56] References Cited

U.S. PATENT DOCUMENTS

| | | |
|---|---|---|
| 5,062,942 | 11/1991 | Kambara et al. . |
| 5,162,654 | 11/1992 | Kostichka et al. . |
| 5,277,780 | 1/1994 | Kambara ............ 204/299 R |
| 5,290,419 | 3/1994 | Kambara et al. ........ 356/344 X |
| 5,307,148 | 4/1994 | Kambara et al. ............ 356/344 |

FOREIGN PATENT DOCUMENTS

| | | |
|---|---|---|
| 0314045 | 5/1989 | European Pat. Off. . |
| 3618605 | 12/1987 | Germany . |

OTHER PUBLICATIONS

Smith et al., "Fluorescence Detection in Automated DNA Sequence Analysis", Nature, vol. 321, No. 12, Jun. 1986, pp. 674–679.

Primary Examiner—Carolyn E. Fields
Assistant Examiner—Edward J. Glick
Attorney, Agent, or Firm—Antonelli, Terry, Stout & Kraus

[57] ABSTRACT

An electrophoresis analyzer includes a light detector for detecting images of a linear fluorescence emitting region, the linear fluorescence emitting region including a plurality of fluorescence emitting points disposed along a straight line, each of the fluorescence emitting points being a point at which samples emit light including a plurality of wavelengths, the light detector including a line sensor, the line sensor including a plurality of photopixels disposed along a straight line, the photopixels constituting a detection surface of the line sensor, an image forming unit for receiving the light emitted by the samples at the fluorescence emitting points and forming a plurality of images of each of the fluorescence emitting points on the detection surface of the line sensor at mutually different positions disposed at a predetermined interval along the straight line along which the photopixels are disposed, and a filter unit disposed between the linear fluorescence emitting region and the light detector for selectively filtering the light emitted by the samples at the fluorescence emitting points such that the images of each of the fluorescence emitting points are formed by light including mutually different ones of the wavelengths.

20 Claims, 6 Drawing Sheets

ELECTROPHORESIS ANALYZER WITH WAVELENGTH SELECTIVE DETECTION

BACKGROUND OF THE INVENTION

The present invention relates to an electrophoresis analyzer with wavelength selective detection and more particularly to an electrophoresis analyzer with wavelength selective detection which is suited to an electrophoresis analysis apparatus for DNA, RNA, or protein.

To analyze DNA, a method for labeling a sample by a fluorophore and optically detecting and analyzing the sample which is electrophoretically separated is used. To compare and analyze various types of samples or increase the throughput of analysis, it is necessary to label a plurality of types of samples respectively by using a plurality of fluorophores with different light emitting wavelengths as labeling fluorophores and to separate and analyze a plurality of types of samples at the same time. In this case, it is necessary to separate and detect the wavelength of fluorescence from each fluorophore. However, generally by using a color filter wheel having a plurality of filters through which light with a predetermined wavelength can transmit, the wavelength of fluorescence is separated and measured (Nature, 1986, Vol. 321, p. 674).

A conventional gel electrophoresis plate is about 20 cm×40 cm in size and has a linear fluorescence emitting region perpendicular to the electrophoretic direction, which is 10 to 15 cm in length. As a method for efficiently detecting fluorescence from such a linear fluorescence emitting region, a method for using a two-dimensional detector and image splitting prism is proposed (U.S. Pat. No. 5,062,942). This method makes a plurality of images of the fluorescence emitting region which are split vertically using a prism or mirror and focusing lens on the detection surface of the two-dimensional detector. Each image is devised so as to be formed on the detection surface after passing through a filter installed in each optical path and wavelength-separated fluorescence images can be detected.

A capillary array electrophoresis method has been proposed recently as an electrophoresis method for separating and analyzing various types of samples (U.S. Pat. No. 5,277,780). The method is designed to line up many capillaries so as to measure samples and is suited to high-speed and high-throughput measurement. According to this method, the inner diameter and inner gel are slightly different in each capillary, so that the electrophoretic speed is changed even in the same sample. Therefore, it is necessary to determine a molecular weight standard by migrating a marker labeled with a fluorophore different from the fluorophore which is labeled for each sample at the same time.

SUMMARY OF THE INVENTION

A conventional electrophoresis analyzer with wavelength selective detection uses a color filter wheel or an image splitting means and two-dimensional detector. Therefore, when a color filter wheel is used, the analyzer uses a movable part, so that it becomes expensive and failures may be caused easily. When a two-dimensional detector is used, the analyzer becomes expensive and the signal reading speed becomes slow. There is a line sensor as a detector with a fast reading speed which is low in price. However, the conventional image splitting method cannot be used for it unlike the two-dimensional detector.

An object of the present invention is to eliminate the difficulties of the prior art mentioned above and to provide an electrophoresis analyzer with wavelength selective detection which is low in price and hard to fail, can read signals at high speed, and is used for an electrophoresis analysis apparatus.

The electrophoresis analyzer with wavelength selective detection of the present invention makes fluorescence images of the measurement target which consists of the linear fluorescence emitting region, which includes a plurality of fluorescence emitting points which are lined on a straight line to which rays of light with different wavelengths are emitted, on the line sensor as a plurality of linear fluorescence images with different wavelengths. In this case, the rays of light emitted from the above fluorescence emitting points are separated by wavelength and focused on the line sensor as spots. A plurality of fluorescence images consisting of these spots are formed in the direction where photopixels of the line sensor are arranged linearly (hereinafter abbreviated to the "sensor direction") so that they do not overlap each other.

Namely, according to the present invention, in an electrophoresis analyzer with wavelength selective detection including a measurement target portion with plural points emitting various fluorescence and being arranged linearly, an image splitting means for making a plurality of fluorescence images of the target on the fluorescence detector, and filters having different transmission wavelengths, a line sensor, where a plurality of photopixels are arranged linearly, is used as a fluorescence detector and a plurality of fluorescence images of the target are formed on the detector so that they are shifted at a predetermined distance in the sensor direction so as to prevent fluorescence images at the fluorescence emitting points from overlapping each other.

The distance at which fluorescence images of the target are shifted may be almost equal to the length of fluorescence images of the target or may be shorter than the distance between fluorescence images at neighboring fluorescence emitting points in the target.

The image splitting means may consist of prisms which are inclined in a direction parallel to the sensor direction and accumulated vertically, or a polygon prism having a ridgeline perpendicular to the sensor direction or a plurality of mirrors in which the reflecting directions to the part to be measured are different from each other.

The effective length of the measurement target is determined as dividing the measurable target length of the detector by the number of fluorophore species. When the length of the measurement target is longer than the effective length, images (partially) overlap each other, which disturbs the wavelength selective measurement. Therefore, a slit is installed in the optical path so as to limit the region of the part to be measured. The electrophoresis analyzer with wavelength selective detection of the present invention can be used as a detection device of an electrophoresis analysis apparatus for separating and analyzing a plurality of samples using a plurality of fluorophores. The image splitting mirror or image splitting prism makes a plurality of linear fluorescence images of the measurement target on the detection surface of the detector so that they are shifted to prevent overlapping each other. Linear fluorescence images are not shifted perpendicularly to the fluorescence images but in the transverse direction on the same line.

These fluorescence images are formed on the detector after passing through filters having different transmission wavelengths via the lens. Since each fluorescence image is lined on a straight line, all the fluorescence images can be detected by a linear line sensor. Namely, all the photopixels of the linear line sensor are divided into a plurality of groups for detecting fluorescence with different wavelengths. One fluorescence emitting point at the part to be measured is imaged as a plurality of points on the line sensor and the fluorescence wavelength at each point is determined by the corresponding filter.

When fluorescence images of the target are shifted at a distance which is almost equal to the length of a fluorescence target image by an image splitting means, fluorescence target images with different wavelengths are formed on the line sensor in the transverse direction. The number of the target images is determined by the number of selecting wavelengths. When fluorescence target images are shifted at a distance which is shorter than the target length and the distance between neighboring fluorescence emitting points in the target, the divided fluorescence emitting points produced with an image splitting means appear between the neighboring fluorescence emitting points on the line sensor as a set of fluorescence images with different wavelengths at the fluorescence emitting points in the transverse direction.

DESCRIPTION OF THE PREFERRED EMBODIMENTS

Embodiment 1

The present invention will be explained using an example that the present invention is used to sequence the base order of DNA, that is, the present invention is applied to an electrophoresis analysis apparatus for separating and analyzing the samples labeled with four types of fouorophores.

Figure 1A:
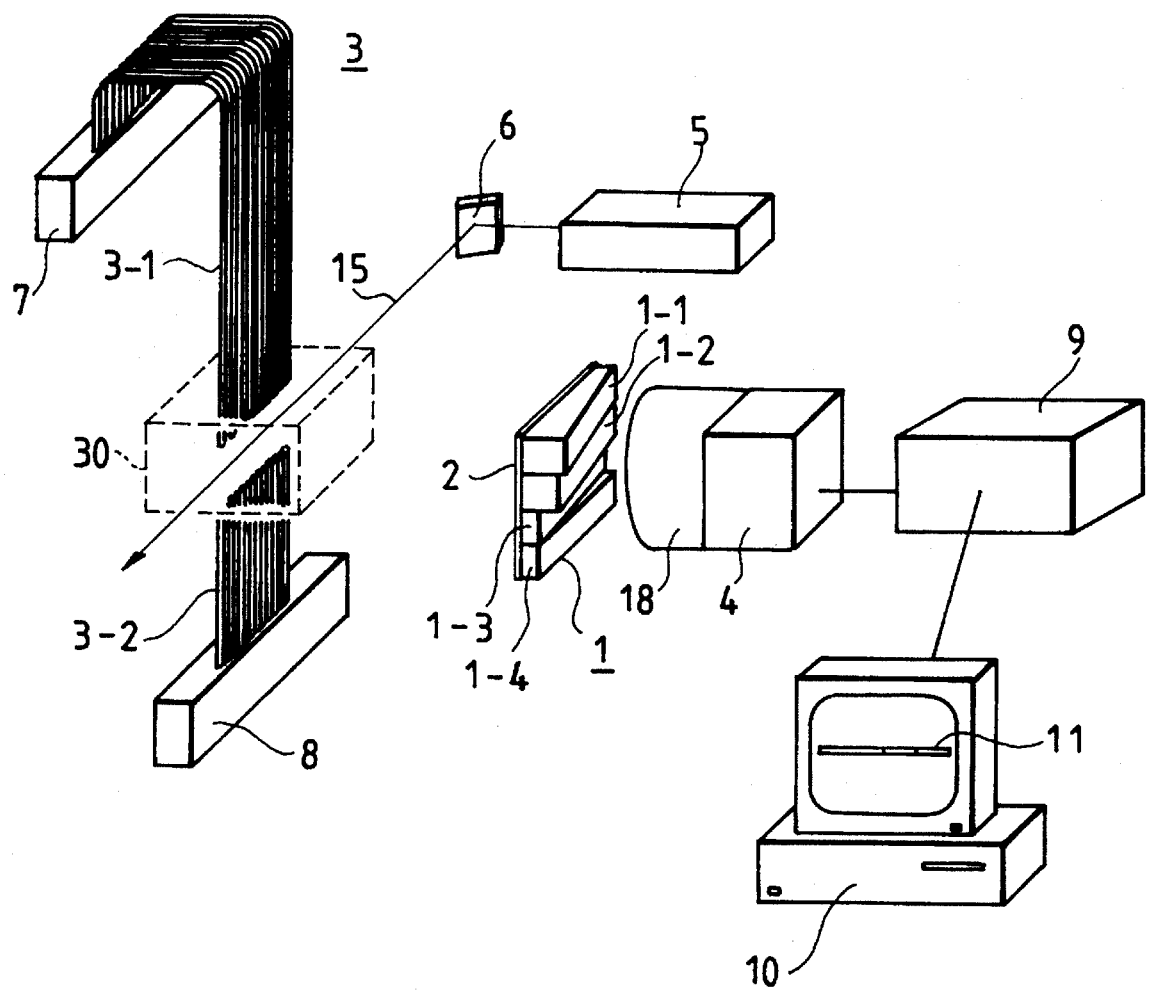
FIG. 1A is a conceptual diagram of an electrophoresis analysis apparatus in which an electrophoresis analyzer with wavelength selective detection of an embodiment of the present invention is incorporated.

FIG. 1A shows an outline of an electrophoresis analysis apparatus in which an electrophoresis analyzer with wavelength selective detection in an embodiment of the present invention is incorporated.

Figure 1B:
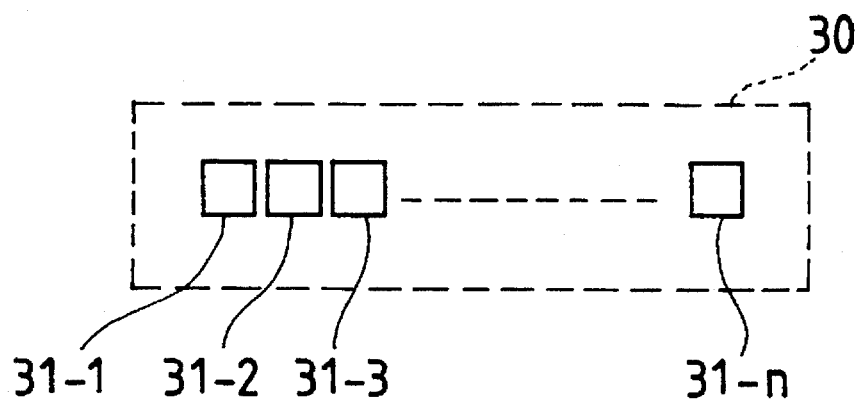
FIG. 1B is a conceptual diagram showing a linear fluorescence emitting region.

The electrophoresis unit consists of a capillary array electrophoresis unit 3. A sample which is injected into the upper end of each upper capillary 3-1 by the electrophoretical injection method is migrated from an upper buffer bath 7 to a lower buffer bath 8 by an electrophoretical voltage applied between the upper buffer bath 7 and the lower buffer bath 8. The sample which is eluted from the upper capillary end enters into an optical cell 30 to be irradiated by a light. The sample flows into the lower open capillary 3-2 with a sheathflow of buffer solution in the optical cell 30. A light beam 15 from a laser 5 is reflected by a mirror 6 and irradiated to the optical cell 30. The above light beam simultaneously irradiates the sample eluted from each capillary end of the upper capillary array 3-1. By irradiation of this light beam, fluorophore labeled DNA existing in the irradiated region emit fluorescence. In the optical path of the light beam, a linear fluorescence emitting region consisting of a plurality of fluorescence emitting points which are emitted from the fluorophores is formed. FIG. 1B shows a conceptual diagram of a linear fluorescence emitting region to be formed. Fluorescence emitting points 31-1 to 31-n, which are lined linearly at an almost equal interval in the optical cell 30, are produced by irradiating fluorophores labeling samples. The fluorescence emitting points make a linear fluorescence emitting region.

The fluorescence from the emitting region (measurement target) is focused and divided by an image splitting means into four linear fluorescence images on a line sensor 4. The image splitting means is an image splitting prism 1 consisting of four prisms and a lens 18. A filter 2 having a different transmission wavelength is installed in front of each prism, so that the four fluorescence images focused on the line sensor 4 are formed by fluorescences with different wavelengths.

A second harmonic wave (5 m W) of a YAG laser with a wavelength of 532 nm is used as excitation light in this embodiment. Erythrosin isothiocyanate (emission wavelength 560 nm), tetramethyl rhodamine isothiocyanate (TRITC, emission wavelength 572 nm), rhodamine X (emission wavelength 602 nm), and sulforhodamine 101 (Texas Red, emission wavelength 620 nm) are used as fluorophores. DNA fragment families having A, T, G or C base terminus for which a predetermined one of the above fluorophores is labeled respective to the base species, are mixed and used as a sample. Needless to say, a combination of another laser and fluorophores may be used. Each filter is an interference filter made of dielectric layers which is a band pass filter in which the central transmission wavelength matches with the light emitting wavelength of each of the above fluorophores. A color glass filter for blocking off scattered light is used and the band pass filter is fixed to the surface of the color glass filter.

The line sensor 4 is installed so that the sensor direction coincides with the direction of the light beam in the optical cell and wavelength separated fluorescences are focused on the line sensor 4 as linear fluorescence images respectively. The inlet surface of the image splitting prism 1 is on the same plane and each of the outlet surfaces has a different inclination to the sensor direction. Four linear fluorescence images are formed on the line sensor 4 without overlapping by the image splitting prism 1. Therefore, a plurality of fluorophores can be detected using the line sensor 4.

As mentioned above, according to this embodiment, only by using a line sensor, no movable part is required by the analyzer and fluorescences from four types of fluorophores can be measured separately. The fluorescence signal detected by the line sensor 4 is transferred to a data processor 10 via a control circuit 9. The data processor 10 displays four splitted fluorescence images 11 on the monitor screen, separates signals of individual fluorophores from the obtained fluorescence signals (emission wavelengths of fluorophores overlap each other in the emission spectra) of four wavelengths caused by the sample eluted from each capillary, that is, the signal intensities at the corresponding locations of the four split fluorescence images, converts and displays the spectra to a signal from each fluorophore, and performs an operation for obtaining a pattern that each fluorescence signal is changed in each time.

Figure 2:
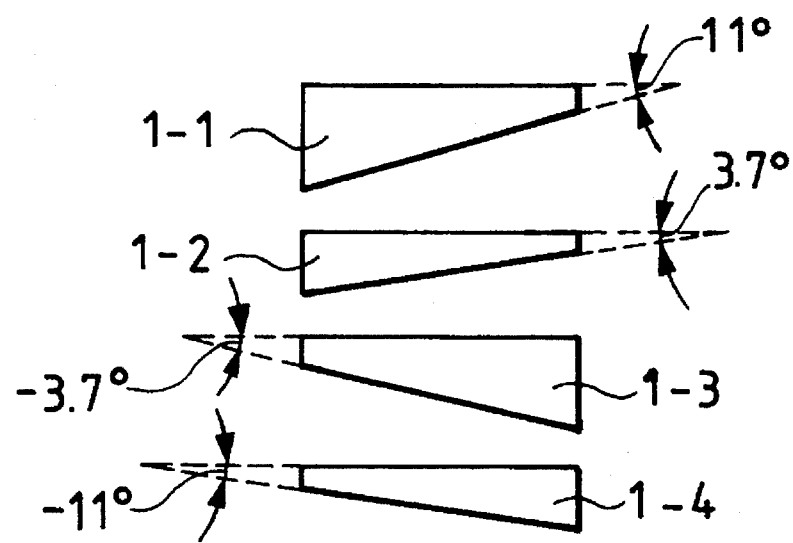
FIG. 2 is a cross sectional view of each prism constituting the image splitting prism used in the embodiment shown in FIG. 1.

FIG. 2 shows a cross sectional view of the components (1-1 to 1-4) of the image splitting prism 1 shown in FIG. 1A. The image splitting prism 1 is used to deflect fluorescence emitted from samples eluted from the capillary array, and to focus them on the line sensor as four fluorescence images lined on a straight line. In the embodiment shown in FIG. 2, the image splitting prism consists of four component prisms having different slopes. Each component prism has an inlet surface which is on the same plane and an outlet surface having a different slope to the sensor direction and the four component prisms are designed so that four fluorescence images are lined on the line sensor in the transverse direction without overlapping each other.

Figure 3A:
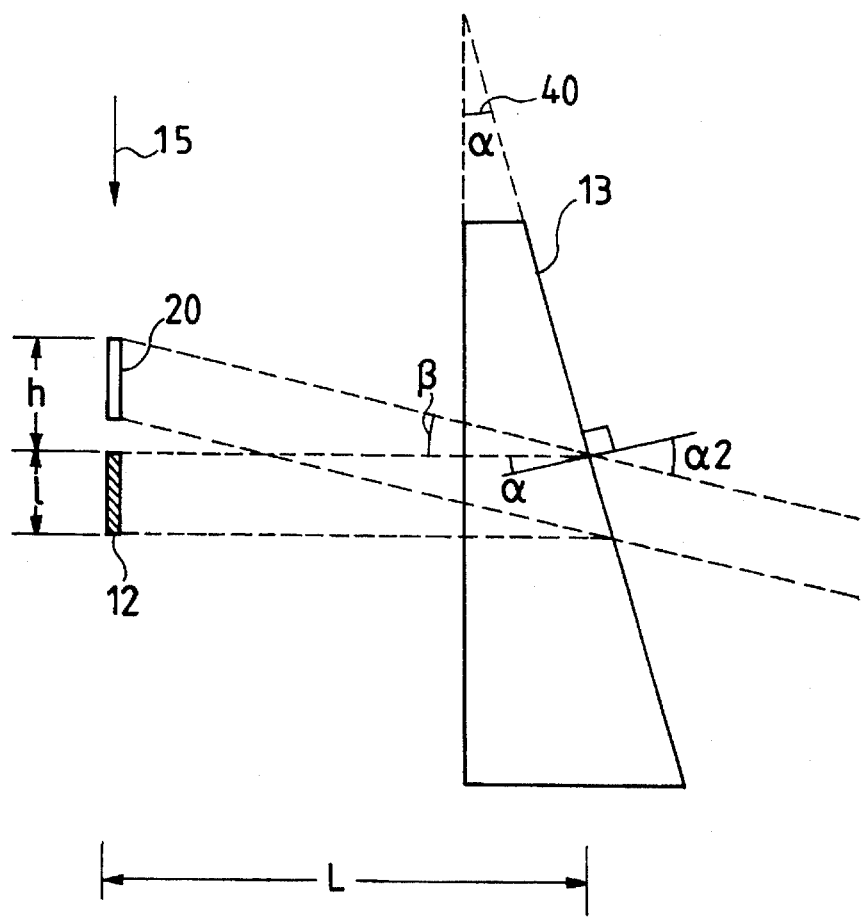
FIG. 3A is an illustration for splitting of an image by a prism.

FIG. 3A illustrates the principle of light refraction in the image splitting prism. A virtual image is formed when fluorescence is refracted by the prism. For simplicity, one prism will be considered. It is assumed that a vertical angle 40 of a prism 13 is $\alpha$ and the refraction index of the material of the prism is n. The prism 13 is placed close to the focusing lens and it is assumed that the distance between the prism and the measurement target 12 is L and the length of the measurement target is l. The measurement target 12 with a length of l is detected as a virtual image 20 of a measurement target which is displaced by a distance h from the original measurement target 12 by the prism 13. Where, h=$\beta$·L. By using the refraction index n of the prism material, the outgoing angle $\alpha_2$ can be approximated to n$\alpha$. Since $\beta=\alpha_2-\alpha=(n-1)\alpha$, h can be approximated to $(n-1)\alpha$·L. To prevent the virtual image 20 from overlapping with the measurement target 12, it is necessary that h$\geq$l and $\alpha$ (angle of the prism 13) $\geq$l/(n-1)L. By using such component prisms, fluorescence images of the measurement target can be formed on the line sensor so that a fluorescence image which is formed via the first prism 1-1 and a fluorescence image which is formed via another prism (1-2 to 1-4) do not overlap each other on the detector.

In this embodiment, component prisms made from a material of borosilicate glass with a refraction index n of 1.52 are used. As a line sensor, an S2301-512 Q type CCD linear image sensor with a length of detecting region of 25.6 mm manufactured by Hamamatsu Photonix, Ltd. is used. The length of the measurement target is 18 min. The focusing lens is a camera lens with F 1.2 (f=50 mm). The distance between the measurement target and the lens is 300 mm and the image magnification factor is 1/5. The image splitting prism is installed in the neighborhood of the focusing lens and L=270 mm.

Figure 3B:
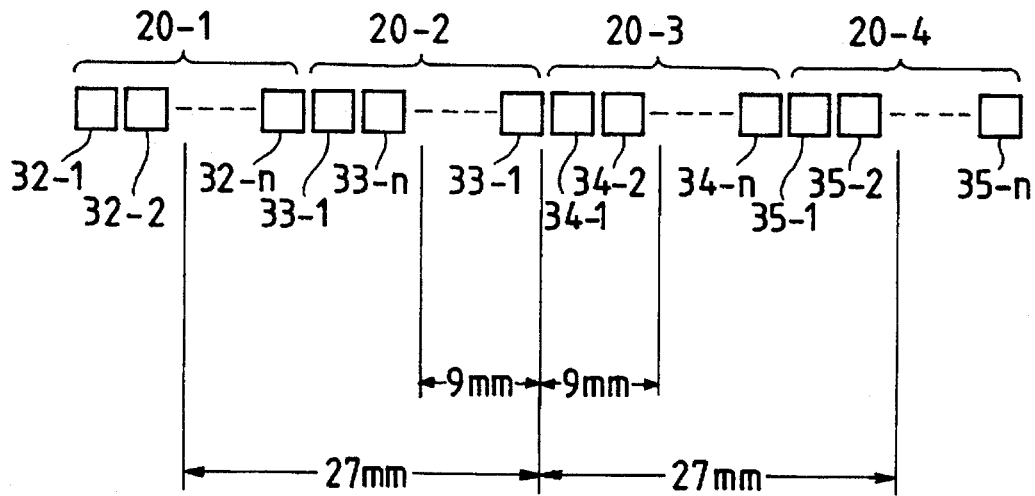
FIG. 3B is a drawing showing an example of a virtual image of a part to be measured.

FIG. 2 shows cross sectional views of the four prisms 1-1 to 1-4. The vertical angles of the four prisms 1-1 to 1-4 are 11°, 3.7°, -3.7°, and -11° respectively. The negative angles mean that the directions of the vertical angles of the prisms 1-3 and 1-4 are opposite to those of the prisms 1-1 and 1-2 which have positive angles against the sensor direction of the line sensor. FIG. 3B shows four virtual images of the measurement target which are generated by four prisms when the measurement target is 18 mm in length. The measurement target is converted to four virtual images 20-1 to 20-4 of which the centers are located at 27 mm, 9 mm, -9 mm, and -27 mm, respectively, from the center of the measurement target.

The four virtual images 20-1 to 20-4 contains virtual dot images 32-1 to 32-n, 33-1 to 33-n, 34-1 to 34-n, and 35-1 to 35-n of the measurement target which contains fluorescence emitting points 31-1 to 31-n (shown in FIG. 1B) in the optical cell 30. The virtual images of the fluorescence emitting points forming each virtual image 20-1 to 20-4 of the measurement target are formed by fluorescence different for each virtual image. The virtual images 32-1, 33-1, 34-1, and 35-1 correspond to the fluorescence emitting point 31-1 and the virtual images (32-2, 33-2, 34-2, and 35-2) to (32-n, 33-n, 34-n, and 35-n) correspond to the other fluorescence emitting points 31-2 to 31-n respectively in the same way.

Embodiment 2

Figure 4A:
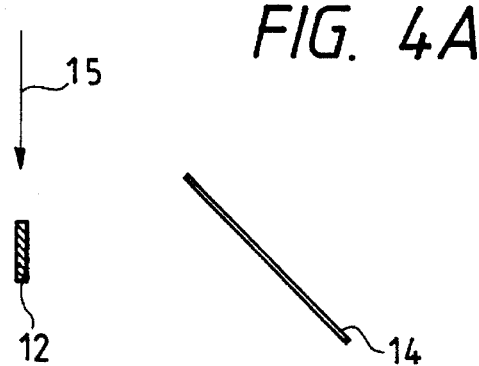
FIG. 4A is a conceptual diagram of an embodiment using a splitting mirror.
Figure 4A:
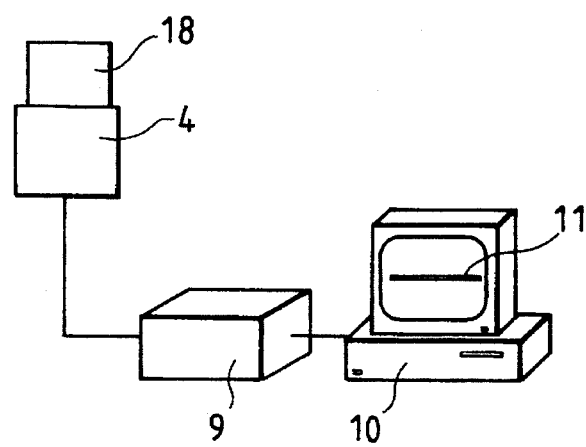

FIG. 4A shows another embodiment of the present invention.

Figure 4B:
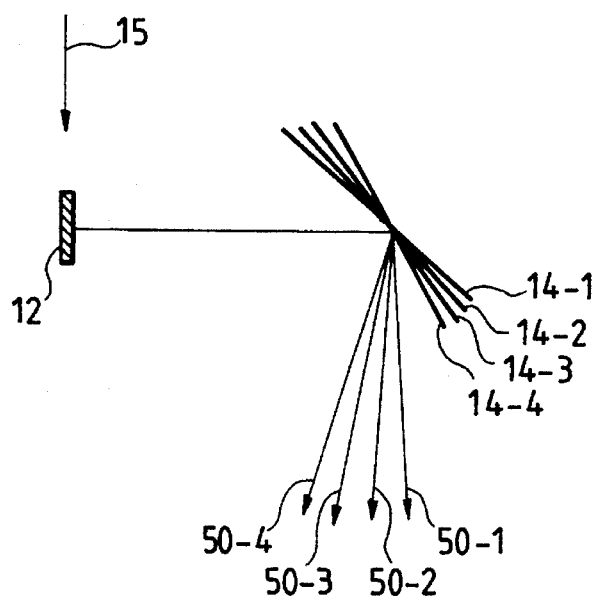
FIG. 4B is a drawing showing details of the splitting mirror shown in FIG. 4A.
Figure 4C:
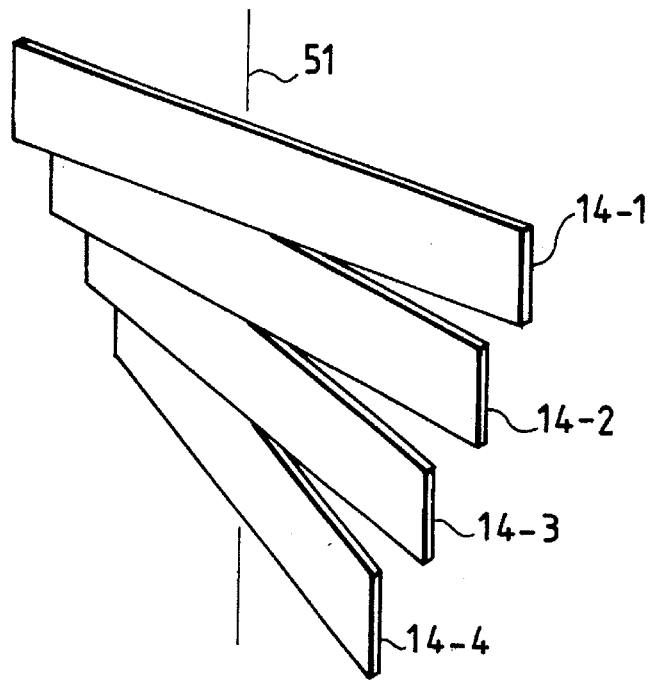
FIG. 4C is a perspective view of the splitting mirror shown in FIG. 4A.

In this embodiment, images are split by a reflection mirror 14 instead of the prism 1 shown in FIG. 1A. FIG. 4B shows details of the image splitting mirror 14 and FIG. 4C shows a perspective view of the image splitting mirror 14. In FIGS. 4B and 4C, to emphasize the relationship between each mirror, the angle between each mirror is emphasized and drawn. The image splitting mirror 14 consists of four mirrors 14-1 to 14-4 having different reflection directions of the measurement target respectively and the reflection directions can be changed around an axis 51. The fluorescence emitted from the measurement target consisting of a plurality of fluorescence emitting points is reflected in different directions 50-1 to 50-4 by the image splitting mirrors 14-1 to 14-4 and focused on a CCD line sensor 4 by a lens 18 as four linear fluorescence images. Band pass filters having different transmission wavelengths which are not shown in the drawings are arranged between the measurement target and the detector, respectively, to select the fluorescence emitted from each fluorophore in wavelength. An output signal from the line sensor 4 is transferred to a data processor 10 via a control circuit 9 and the data processing described in Embodiment 1 is performed.

Figure 4D:
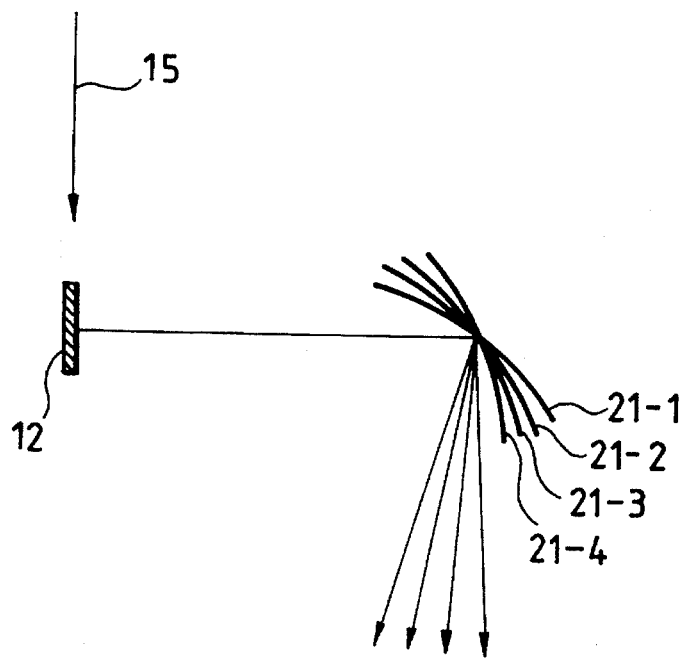
FIG. 4D is a drawing showing a concave mirror of another embodiment.

The image splitting mirror 14 in this embodiment can be manufactured at a lower price than the image splitting prism described in the first embodiment. As image splitting mirrors, curved mirrors 21-1 to 21-4 having the focusing operation shown in the plan view in FIG. 4D can be used. The curved mirrors 21-1 to 21-4 are installed so that they reflect fluorescences from the measurement target in different directions in the same way as the rectangular mirror 14. By using these curved mirrors 21-1 to 21-4, the measurement target consisting of a plurality of fluorescence emitting points can be reflected in different directions and focused on the CCD line sensor 4 without focusing lens as four linear fluorescence images. An output signal from the line sensor 4 is transferred to the data processor 10 via the control circuit 9 and the data processing described in Embodiment 1 is performed.

Embodiment 3

Figure 5:
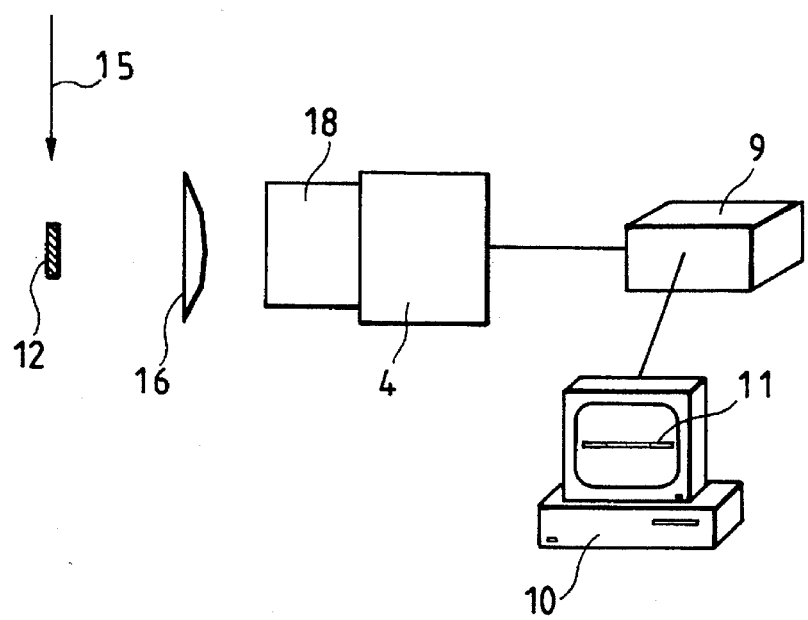
FIG. 5 is a conceptual diagram of an embodiment using a polygon prism.
Figure 6:
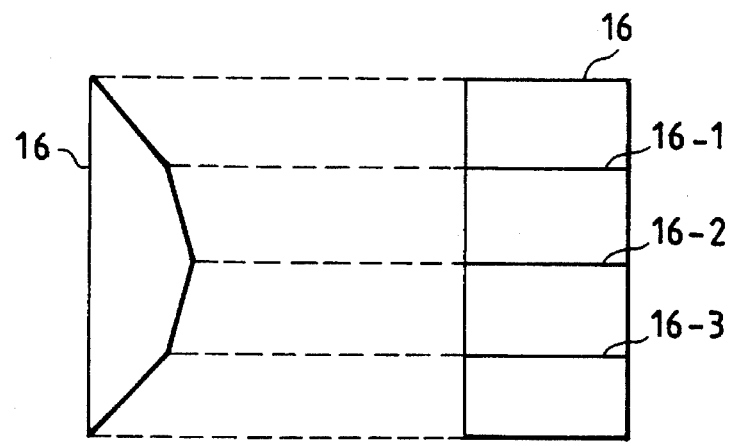
FIG. 6 is an enlarged drawing of the polygon prism.

FIG. 5 shows another embodiment of the present invention. In this embodiment, an integrated polygon prism 16 is used instead of the prisms 1 which overlay each other vertically as shown in FIG. 1A as an image splitting prism. FIG. 6 shows an enlarged view of the polygon prism 16. The polygon prism 16 has an inlet surface and four outlet surfaces which are divided by ridgelines 16-1 to 16-3 perpendicular to the sensor direction of the line sensor 4. In the same way as with the aforementioned embodiment, the fluorescence emitted from the measurement target which is generated by irradiation of the laser beam 15 is focused into four linear fluorescence images which are located side by side in the sensor direction on the detection surface of the line sensor 4 by the image splitting prism 16 and the lens 18. Between the measurement target and the CCD line sensor 4, a band pass filter for selecting the fluorescence wavelength of each fluorescence image is installed. An output signal from the line sensor 4 is transferred to the data processor 10 via the control circuit 9 and the data processing described in Embodiment 1 is performed.

Figure 7:
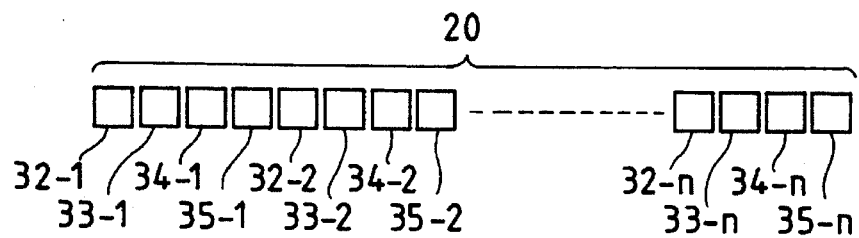
FIG. 7 is a drawing showing another example of a virtual image of the part to be measured.

In each embodiment mentioned above, a case that four types of fluorophores are detected is explained. However, needless to say, the numbers of prisms, outlet surfaces of the polygon prism, reflection mirrors, and filters to be used together may be optionally increased or decreased according to the number of types of fluorophores. According to each embodiment mentioned above, a linear fluorescence image with a predetermined length is split into fluorescence images which are focused on the detector separately with shifting the center positions of the images by the length thereof and separated into various wavelengths, and detected. However, the interval between each neighboring capillaries may be made wider so as to allow the splitted fluorescence images of each fluorescence emitting point in the measurement target to be adjacent to one another and form a set of image points consisting various wavelength fluorescence from the same fluorescence emitting point. In this case, the distance at which fluorescence images of the measurement target are shifted in the sensor direction is shorter than the distance between fluorescence images at neighboring fluorescence emitting points in the measurement target and the shifting distance of fluorescence images may be about 0.5 to 2 mm. FIG. 7 shows a virtual image of the measurement target. A virtual image 20 of the measurement target consists of a plurality of virtual images at a plurality of fluorescence emitting points 31-1 to 31-n (shown in FIG. 1B) in the optical cell 30. Four virtual images 32-1, 33-1, 34-1, and 35-1 which are formed for fluorescences with different wavelengths corresponding to a fluorescence emitting point 31-1 are lined sequentially. Next, four virtual images 32-2, 33-2, 34-2, and 35-2 which are formed for fluorescences with different wavelengths corresponding to the fluorescence emitting point 31-2 are lined sequentially. Also for the fluorescence emitting points 31-3 to 31-n, four virtual images which are formed for fluorescences with different wavelengths are lined sequentially.

The electrophoresis analyzer with wavelength selective detection of the present invention can be applied to a system having migration tracks made of grooves which are formed on a glass plate by etching or migration tracks formed in a slab gel in addition to capillary array migration tracks.

Furthermore, the electrophoresis analyzer with wavelength selective detection of the present invention can be applied to any apparatus which detects rays of light with a plurality of wavelengths from a linear part to be measured practically at the same time in addition to an electrophoresis analysis apparatus. For example, the electrophoresis analyzer with wavelength selective detection can be applied to an apparatus consisting of a plurality of flow cells which are arranged in array and of a plurality of fluorophores or fluorophore labeled samples to flow into these flow cells.

As mentioned above, according to the present invention, neither a movable part nor a two-dimensional detector are necessary and rays of light with a plurality of types of wavelengths can be detected using a line sensor. Therefore, samples can be labeled by a plurality of types of fluorophores and analyzed, so that an analysis apparatus for DNA or others which is small-sized, light in weight, hard to fail, low-priced, and speedy can be realized.

What is claimed is:

1. An electrophoresis analyzer comprising:

a light detector for detecting images of a linear fluorescence emitting region, the linear fluorescence emitting region including a plurality of fluorescence emitting points disposed along a straight line, each of the fluorescence emitting points being a point at which samples emit light including a plurality of wavelengths, the light detector including a line sensor, the line sensor including a plurality of photopixels disposed along a straight line, the photopixels constituting a detection surface of the line sensor;

image forming means for receiving the light emitted by the samples at the fluorescence emitting points and forming a plurality of images of each of the fluorescence emitting points on the detection surface of the line sensor at mutually different positions disposed at a predetermined interval along the straight line along which the photopixels are disposed; and filter means disposed between the linear fluorescence emitting region and the light detector for selectively filtering the light emitted by the samples at the fluorescence emitting points such that the images of each of the fluorescence emitting points are formed by light including mutually different ones of the wavelengths.

2. An electrophoresis analyzer according to claim 1, wherein the predetermined interval is substantially equal to a length of the linear fluorescence emitting region viewed from the detection surface of the line sensor through the image forming means.

3. An electrophoresis analyzer according to claim 1, wherein the predetermined interval is less than a distance between adjacent ones of the fluorescence emitting points viewed from the detection surface of the line sensor through the image forming means.

4. An electrophoresis analyzer according to claim 1, wherein the image forming means includes one of:

(1) a plurality of prisms disposed in a direction perpendicular to the straight line along which the photopixels are disposed;

(2) a polygon prism having a plurality of ridgelines each extending in a direction perpendicular to the straight line along which the photopixels are disposed; and (3) a plurality of mirrors for received the light emitted by the samples at the fluorescence emitting points and reflecting the received light in a plurality of mutually different directions, the mirrors being one of flat mirrors and concave mirrors.

5. An electrophoresis analyzer according to claim 1, wherein the samples are fluorophores or are labeled with fluorophores;

wherein the light emitted by the samples is fluorescence emitted by the fluorophores; and wherein the electrophoresis analyzer further comprises:

laser beam irradiating means for irradiating the linear fluorescence emitting region with a laser beam along the straight line along which the fluorescence emitting points are disposed to excite the fluorophores when the samples are at the fluorescence emitting points, thereby causing the fluorophores to emit the fluorescence.

6. An electrophoresis analyzer according to claim 1, wherein the samples are fluorophores or are labeled with fluorophores;

wherein the light emitted by the samples is fluorescence emitted by the fluorophores;

wherein the samples migrate in a migration direction along a plurality of electrophoretic migration tracks; and wherein the straight line along which the fluorescence emitting points are disposed extends in a direction perpendicular to the migration direction.

7. An electrophoresis analyzer according to claim 1, wherein the samples are fluorophores or are labeled with fluorophores;

wherein the light emitted by the samples is fluorescence emitted by the fluorophores;

wherein the samples migrate in a migration direction along a plurality of electrophoretic migration tracks; and wherein the straight line along which the fluorescence emitting points are disposed extends outside the electrophoretic migration tracks past respective ends of the electrophoretic migration tracks.

8. An electrophoresis analyzer according to claim 1, wherein the samples are fluorophores or are labeled with fluorophores;

wherein the light emitted by the samples is fluorescence emitted by the fluorophores;

wherein the samples migrate in a migration direction along a plurality of migration tracks disposed in respective capillaries; and wherein the straight line along which the fluorescence emitting points are disposed extends in a direction perpendicular to the migration direction.

9. An electrophoresis analyzer according to claim 1, wherein the samples are fluorophores or are labeled with fluorophores;

wherein the light emitted by the samples is fluorescence emitted by the fluorophores;

wherein the samples migrate in a migration direction along a plurality of electrophoretic migration tracks disposed in respective capillaries; and wherein the straight line along which the fluorescence emitting points are disposed extends outside the capillaries past respective ends of the capillaries.

10. An electrophoresis analyzer according to claim 1, wherein the samples are fluorophores or are labeled with fluorophores;

wherein the light emitted by the samples is fluorescence emitted by the fluorophores;

wherein the samples migrate in a migration direction along a plurality of migration tracks disposed in respective capillaries;

wherein the straight line along which the fluorescence emitting points are disposed extends in a direction perpendicular to the migration direction; and wherein the image forming means includes one of:
  (1) a plurality of prisms disposed in a direction perpendicular to the straight line along which the photopixels are disposed;
  (2) a polygon prism having a plurality of ridgelines each extending in a direction perpendicular to the straight line along which the photopixels are disposed; and
  (3) a plurality of mirrors for receiving the light emitted by the samples at the fluorescence emitting points and reflecting the received light in a plurality of mutually different directions.

11. An electrophoresis analyzer according to claim 1, wherein the samples are fluorophores or are labeled with fluorophores;

wherein the light emitted by the samples is fluorescence emitted by the fluorophores;

wherein the samples migrate in a migration direction along a plurality of electrophoretic migration tracks disposed in respective capillaries; and wherein the straight line along which the fluorescence emitting points are disposed extends outside the capillaries past respective ends of the capillaries; and wherein the image forming means includes one of:
  (1) a plurality of prisms disposed in a direction perpendicular to the straight line along which the photopixels are disposed;
  (2) a polygon prism having a plurality of ridgelines each extending in a direction perpendicular to the straight line along which the photopixels are disposed; and
  (3) a plurality of mirrors for receiving the light emitted by the samples at the fluorescence emitting points and reflecting the received light in a plurality of mutually different directions.

12. An electrophoresis analyzer comprising:

a light detector for detecting images of a linear fluorescence emitting region, the linear fluorescence emitting region including a plurality of fluorescence emitting points disposed along a straight line, each of the fluorescence emitting points being a point at which samples emit light including a plurality of wavelengths, the light detector including a line sensor, the line sensor including a plurality of photopixels disposed along a straight line, the photopixels constituting a detection surface of the line sensor;

image forming means for receiving the light emitted by the samples at the fluorescence emitting points and forming a plurality of images of each of the fluorescence emitting points on the detection surface of the line sensor at mutually different positions along the straight line along which the photopixels are disposed; and filter means disposed between the linear fluorescence emitting region and the light detector for selectively filtering the light emitted by the samples at the fluorescence emitting points such that the images of each of the fluorescence emitting points are formed by light including mutually different ones of the wavelengths.

13. An electrophoresis analyzer according to 12, wherein the image forming means forms the images of the fluorescence emitting points on the detection surface of the line sensor such that the images of the fluorescence emitting points are divided into a plurality of groups of images of fluorescence emitting points, the groups being disposed along the straight line along which the photopixels are disposed, each of the groups including one image of each of the fluorescence emitting points formed by light including a respective one of the wavelengths.

14. An electrophoresis analyzer according to 12, wherein the image forming means forms the images of the fluorescence emitting points on the detection surface of the line sensor such that the images of the fluorescence emitting points are divided into a plurality of groups of images of fluorescence emitting points, the groups being disposed along the straight line along which the photopixels are disposed, each of the groups including all of the images of a respective one of the fluorescence emitting points.

15. An electrophoresis analyzer comprising:

a light detector for detecting images of a linear fluorescence emitting region, the linear fluorescence emitting region including a plurality of fluorescence emitting points disposed along a straight line, each of the fluorescence emitting points being a point at which samples emit light including a plurality of wavelengths, the light detector including a line sensor, the line sensor including a plurality of photopixels disposed along a straight line, the photopixels constituting a detection surface of the line sensor;

image forming means for receiving the light emitted by the samples at the fluorescence emitting points and forming a plurality of images of each of the fluorescence emitting points on the detection surface of the line sensor at mutually different positions disposed at a predetermined interval along the straight line along which the photopixels are disposed; and first filter means disposed between the linear fluorescence emitting region and the light detector for blocking off scattered light.

16. An electrophoresis analyzer according to claim 15, further comprising second filter means disposed between the linear fluorescence emitting region and the light detector for selectively filtering the light emitted by the samples at the fluorescence emitting points such that the images of each of the fluorescence emitting points are formed by light including mutually different ones of the wavelengths.

17. An electrophoresis analyzer according to claim 15, wherein the image forming means includes one of:

(1) a plurality of prisms disposed in a direction perpendicular to the straight line along which the photopixels are disposed;

(2) a polygon prism having a plurality of ridgelines each extending in a direction perpendicular to the straight line along which the photopixels are disposed; and (3) a plurality of mirrors for receiving the light emitted by the samples at the fluorescence emitting points and reflecting the received light in a plurality of mutually different directions, the mirrors being one of flat mirrors and concave mirrors.

18. An electrophoresis analyzer comprising:

a light detector for detecting images of a linear fluorescence emitting region, the linear fluorescence emitting region including a plurality of fluorescence emitting points disposed along a straight line, each of the fluorescence emitting points being a point at which samples emit light including a plurality of wavelengths, the light detector including a line sensor, the line sensor including a plurality of photopixels disposed along a straight line, the photopixels constituting a detection surface of the line sensor;

image forming means for receiving the light emitted by the samples at the fluorescence emitting points and forming a plurality of images of each of the fluorescence emitting points on the detection surface of the line sensor at mutually different positions along the straight line along which the photopixels are disposed; and first filter means disposed between the linear fluorescence emitting region and the light detector for blocking off scattered light.

19. An electrophoresis analyzer according to claim 18, further comprising second filter means disposed between the linear fluorescence emitting region and the light detector for selectively filtering the light emitted by the samples at the fluorescence emitting points such that the images of each of the fluorescence emitting points are formed by light including mutually different ones of the wavelengths.

20. An electrophoresis analyzer comprising:

a light detector for detecting images of a linear fluorescence emitting region, the linear fluorescence emitting region including a plurality of fluorescence emitting points disposed along a straight line, each of the fluorescence emitting points being a point at which samples emit light including a plurality of wavelengths, the light detector including a line sensor, the line sensor including a plurality of photopixels disposed along a straight line, the photopixels constituting a detection surface of the line sensor;

image forming means for receiving the light emitted by the samples at the fluorescence emitting points and forming a plurality of images of each of the fluorescence emitting points on the detection surface of the line sensor at mutually different positions disposed at a predetermined interval along the straight line along which the photopixels are disposed; and filter means disposed between the linear fluorescence emitting region and the light detector for blocking off scattered light;

wherein the samples are fluorophores or are labeled with fluorophores;

wherein the light emitted by the samples is fluorescence emitted by the fluorophores;

wherein the samples migrate in a migration direction along a plurality of electrophoretic migration tracks; and wherein the straight line along which the fluorescence emitting points are disposed extends in a direction perpendicular to the migration direction.

* * * * *